United States Patent
Aljalal et al.

(10) Patent No.: US 11,162,927 B2
(45) Date of Patent: *Nov. 2, 2021

(54) NO2 CONCENTRATION MEASURMENT METHOD USING MULTIMODE LASER BEAM

(71) Applicant: KING FAHD UNIVERSITY OF PETROLEUM AND MINERALS, Dhahran (SA)

(72) Inventors: Abdulaziz Aljalal, Dhahran (SA); Sameh Altanany, Dhahran (SA); Khaled Gasmi, Dhahran (SA); Watheq Al-Basheer, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 112 days.

This patent is subject to a terminal disclaimer.

(21) Appl. No.: 16/789,692

(22) Filed: Feb. 13, 2020

(65) Prior Publication Data
US 2020/0182844 A1  Jun. 11, 2020

Related U.S. Application Data

(63) Continuation of application No. 15/962,564, filed on Apr. 25, 2018.

(51) Int. Cl.
*G01N 33/00* (2006.01)
*G01N 21/31* (2006.01)
(Continued)

(52) U.S. Cl.
CPC ....... *G01N 33/0037* (2013.01); *G01N 21/314* (2013.01); *G01N 21/39* (2013.01); *G01N 21/61* (2013.01); *G01N 2021/3155* (2013.01)

(58) Field of Classification Search
CPC .. G01N 33/0037; G01N 21/314; G01N 21/39; G01N 21/61
See application file for complete search history.

(56) References Cited

U.S. PATENT DOCUMENTS

| | | |
|---|---|---|
| 7,616,316 B1 | 11/2009 | Silver et al. |
| 8,390,813 B2 | 3/2013 | Clegg et al. |
| (Continued) | | |

FOREIGN PATENT DOCUMENTS

| | | |
|---|---|---|
| AU | 2014215941 B2 | 9/2014 |
| JP | 59-57143 | 4/1984 |

OTHER PUBLICATIONS

Michael Fernez, et al., "Real-time measurement of the $NO_2$ concentration in ambient air using a multi-mode diode laser and cavity enhanced multiple line integrated absorption spectroscopy", Proceedings SPIE vol. 9486, Advanced Environmental, Chemical, and Biological Sensing Technologies XII, May 13, 2015, 1 page.

(Continued)

*Primary Examiner* — Rebecca C Bryant
(74) *Attorney, Agent, or Firm* — Oblon, McClelland, Maier & Neustadt, L.L.P.

(57) ABSTRACT

A method of measuring a concentration of $NO_2$ in a gaseous mixture using a multimode laser beam that covers a tunable spectral range with a width of no more than 5 nm, wherein the multimode laser beam provides a high resolution transmittance spectrum at an absorption cross section of $NO_2$ molecules, and a system for measuring the concentration of $NO_2$ in the gaseous mixture. Various combinations of embodiments of the system and the method are provided.

14 Claims, 4 Drawing Sheets

(51) Int. Cl.
*G01N 21/39* (2006.01)
*G01N 21/61* (2006.01)

(56) References Cited

U.S. PATENT DOCUMENTS

| | | |
|---|---|---|
| 2007/0081162 A1 | 4/2007 | Roller et al. |
| 2012/0062895 A1 | 3/2012 | Rao et al. |
| 2018/0306713 A1 | 10/2018 | Rao et al. |
| 2019/0195781 A1 | 6/2019 | Waclawek et al. |

OTHER PUBLICATIONS

Feng Xu, et al., "Nitrogen dioxide monitoring using a blue LED", Applied Optics, vol. 47, No. 29, Oct. 7, 2008, pp. 5337-5340.

Hongming Yi, et al., "Application of a broadband blue laser diode to trace $NO_2$ detection using off-beam quartz-enhanced photoacoustic spectroscopy", Optics Letters, vol. 36, No. 4, Feb. 15, 2011, pp. 481-483.

Yutaka Matsumi, et al., "Fluorescence detection of atmospheric nitrogen dioxide using a blue light-emitting diode as an excitation source", Applied Optics, vol. 49, No. 19, Jun. 28, 2010, pp. 3762-3767.

Jacek Wojtas, et al., "Aspects of the Application of Cavity Enhanced Spectroscopy to Nitrogen Oxides Detection", Sensors, vol. 13, Jun. 10, 2013, pp. 7570-7598.

Yong Yang, et al., "Detection of nitrogen dioxide using an external modulation diode laser", Applied Optics, vol. 52, No. 13, Apr. 24, 2013, pp. 3027-3030.

J.T.C. Liu, et al. "High-sensitivity absorption diagnostic for $NO_2$ using a blue diode laser", Journal of Quantitative Spectroscopy & Radiative Transfer, vol. 72, 2002, pp. 655-664.

Fumikazu Taketani, et al., "Trace detection of atmospheric $NO_2$ by laser-induced fluorescence using a GaN diode laser and a diode-pumped YAG laser", Applied Optics, vol. 46, No. 6, Feb. 20, 2007, pp. 907-915.

Gabriel Somesfalean, et al., "Long-path monitoring of $NO_2$ with a 635 nm diode laser using frequency-modulation spectroscopy", Applied Optics, vol. 44, No. 24, Aug. 20, 2005, pp. 5148-5151.

NO2 CONCENTRATION MEASURMENT METHOD USING MULTIMODE LASER BEAM

CROSS-REFERENCE TO RELATED APPLICATIONS

The present application is a Continuation of 15/962,564, now allowed, having a filing date of Apr. 25, 2018.

STATEMENT OF FUNDING ACKNOWLEDGEMENT

The funding support provided by King Abdulaziz City for Science and Technology (KACST) through the Science & Technology Unit at King Fahd University of Petroleum & Minerals (KFUPM) for funding this work under project No. 12-ENV2365-04, and Internal Research Grants of King Fand University of Petroleum and Minerals under project No. RG1218-1, RG1218-2, RG1422-1, and RG1422-2 are gratefully acknowledged.

STATEMENT REGARDING PRIOR DISCLOSURES BY THE INVENTOR OR A JOINT INVENTOR

Aljalal et al., *Detection of trace amount of $NO_2$ gas using tunable blue laser diode.* Proceedings of the SPIE, Volume 10231, 102311E, May 16, 2017, which is incorporated by reference in its entirety.

BACKGROUND OF THE INVENTION

Technical Field

The present invention relates to a method of measuring a concentration of $NO_2$ in a gaseous mixture using a multimode laser beam, wherein the multimode laser beam provides a high resolution transmittance spectrum at an absorption cross section of $NO_2$ molecules.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Nitrogen dioxide ($NO_2$) is one of the air pollutants that are released from the combustion of fossil fuel, for example, in car engines or power plants. $NO_2$ is a reactive compound that has a significant influence on the chemistry of the atmosphere [Richter, A., Burrows, J. P., NÜß, H., Granier, C., Niemeier, U., "Increase in tropospheric nitrogen dioxide over China observed from space," Nature 437(618), 129-132 (2005); J. E. Andrews, P. B., T. D. Jickells, P. S. L. and B. R., An Introduction to Environmental Chemistry, Wiley-Blackwell (2004)]. Photochemical reactions involving $NO_2$ generally lead to the formation of harmful chemical compounds in the atmosphere, thus adversely affecting human life and the environment, for example, causing acid rain. In addition, $NO_2$ can react with compounds present in the atmosphere and form carcinogenic compounds and particles that may penetrate sensitive human organs thus causing respiratory diseases [United States Environmental Protection Agency., "Nitrogen Dioxide ($NO_2$) Pollution," 2017].

Two safe exposure limits of $NO_2$ concentration in ambient air are defined by regulatory environmental agencies. The first limit is referred to as a long-term exposure limit, which is an average $NO_2$ concentration over a 1-year period, and the second limit is a short-term exposure limit, which is an average $NO_2$ concentration over a 1-hour period. For instance, the USA Environmental Protection Agency (EPA) has set the long-term exposure limit to 53 ppb and the short-term exposure limit to 100 ppb [United States Environmental Protection Agency., "Nitrogen Dioxide ($NO_2$) Pollution," 2017], and the European Commission Environment has set the long-term exposure limit of 20 ppb [European Commission., "Air Quality Standards," 2016].

Different instruments have been developed for measuring and monitoring the concentration of $NO_2$. These instruments are generally classified as i) point-monitoring instruments that are capable of measuring at specific locations, and ii) long-path monitoring instruments that are capable of remote measurement of $NO_2$ concentrations over extended paths. Point-monitoring instruments generally operate based on chemiluminescence, fluorescence, colorimetry, diffusion, electrochemistry, or electrical resistivity [Liberti, A., "Modern methods for air pollution monitoring," Pure Appl. Chem. 44, 519-534 (1975)]. However, long-path monitoring instruments generally operate based on the absorption cross section of $NO_2$ molecules in the spectral region in the wavelength range of 300-600 nm. Differential Optical Absorption Spectrometers (DOAS), Tunable Diode Laser Absorption Spectrometers (TDLAS), and Differential Absorption LIDAR devices (DIAL) are among these types of instruments [Platt, U., Stutz, J., Differential Optical Absorption Spectroscopy Principles and Applications, Springer (2008); Kormann, R., Fischer, H., Gurk, C., Helleis, F., Klu, T., Kowalski, K., Parchatka, U., Wagner, V., "Application of a multi-laser tunable diode laser absorption spectrometer for atmospheric trace gas measurements at sub-ppbv levels," Spectrochim. Acta Part A 58, 2489-2498 (2002); Menyuk, N., Killinger D. K., DeFeo, W. E., "Remote sensing of NO using a differential absorption lidar," Appl. Opt. 19(19), 3282-3286 (1980)]. Although, DOAS appear to be the most widely used instruments among long-path monitoring instruments [United States Environmental Protection Agency., "List of designated reference and equivalent methods" (2016)], the availability of blue diode lasers makes TDLAS an attractive alternative to DOAS. In contrast to DOAS, TDLAS can generate light beams with higher spectral intensities and greater collimation, thus creating larger signal-to-noise ratios without the need for expensive collimation optical components.

Blue laser diodes have been used to detect $NO_2$ using laser induced fluorescence [Parra, J., George, L. A., Parra, J., George, L. A., "Development of an ambient pressure laser-induced fluorescence instrument for nitrogen dioxide Development of an ambient pressure laser-induced fluorescence instrument for nitrogen dioxide," Appl. Opt. 48(18), 3355-3361 (2009); Taketani, F., Kawai, M., Takahashi, K., Matsumi, Y., "Trace detection of atmospheric $NO_2$ by laser-induced fluorescence using a GaN diode laser and a diode-pumped YAG laser," Appl. Opt. 46(2), 907-915 (2007)1, photoacoustic detection [Yi, H., Liu, K., Chen, W., Tan, T., Wang, L., Gao, X., "Application of a broadband blue laser diode to trace $NO_2$ detection using off-beam quartz-enhanced photoacoustic spectroscopy," Opt. Lett. 10 36(4), 481-483 (2011); Kalkman, J., Kesteren, H. Van., "Relaxation effects and high sensitivity photoacoustic detection of NO$_2$ with a blue," Appl. Opt. 200(2), 197-200 (2008)], cavity-enhanced absorption spectroscopy [Courtillot, I., Morville, J., Motto-ros, V., Romanini, D., "Sub-ppb NO$_2$ detection by optical feedback cavity-enhanced absorption spectroscopy with a blue diode laser," 407-412 (2006); Wojtas, J., Mikolajczyk, J., Bielecki, Z., "Aspects of the Application of Cavity Enhanced Spectroscopy to Nitrogen Oxides Detection," Sensors 13(x), 7570-7598 (2013)1, and single-pass absorption [Liu., J. T. C., Hanson, R. K., Jeffries, J. B., "High-sensitivity absorption diagnostic for NO$_2$ using a blue diode laser," J. Quant. Spectrosc. Radiat. Transf. 72(2), 655-664 (2002); Yang, Y., Gao, Z., Zhong, D., Lin, W., "Detection of nitrogen dioxide using an external modulation diode laser," Appl. Opt. 52(2), 2-5 (2013)].

Employing blue laser diodes provides detection of NO$_2$ in open-air paths at very low detection limits. However, in the blue region, the sharp features of the NO$_2$ absorption spectrum are relatively broad with an average width of a few nanometers. Therefore, detection and concentration measurement of NO$_2$ becomes very challenging when conventional methods of direct or wave-modulated absorption spectroscopy is employed.

In view of the forgoing, one objective of the present disclosure is to provide a method of measuring a concentration of NO$_2$ in a gaseous mixture using a multimode laser beam that covers a tunable spectral range with a width of no more than 5 nm, wherein the multimode laser beam provides a high resolution transmittance spectrum at an absorption cross section of NO$_2$ molecules.

BRIEF SUMMARY OF THE INVENTION

According to a first aspect, the present disclosure relates to a method of measuring a concentration of nitrogen dioxide in a gaseous mixture, involving i) generating a multimode laser beam with a tunable laser diode at an injection current and a diode temperature, ii) splitting the multimode laser beam into a reference beam and a signal beam, iii) passing the signal beam through the gaseous mixture and recording a first voltage signal with a first detector, iv) passing the reference beam through a reference medium and recording a second voltage signal with a second detector, v) measuring a transmittance of the signal beam at the injection current, wherein the transmittance is a ratio of the first voltage signal to the second voltage signal, vi) tuning the multimode laser beam by varying the injection current and repeating the splitting, passing the signal beam, passing the reference beam, and the measuring to form a high resolution transmittance spectrum, vii) measuring a column density of nitrogen dioxide in the gaseous mixture from the high resolution transmittance spectrum, viii) calculating the concentration of nitrogen dioxide in the gaseous mixture from the column density.

In one embodiment, the multimode laser beam has a wavelength in the range of 250-650 nm.

In one embodiment, the multimode laser beam is a blue laser beam with a wavelength in the range of 445-455 nm.

In one embodiment, the multimode laser beam covers a tunable spectral range with a width of no more than 5 nm.

In one embodiment, the tuning is carried out by increasing the injection current from 30 mA to 160 mA with an increment of 0.05-0.2 mA.

In one embodiment, the multimode laser beam is tuned at an injection current resolution of 0.002-0.008 nm/mA.

In one embodiment, the tuning is carried out in a wavelength region with a width of no more than 5 nm.

In one embodiment, the diode temperature is set to a value in the range of 10-60° C. before the splitting.

In one embodiment, the transmittance of the signal beam is measured in a wavelength region of 445-450 nm.

In one embodiment, the transmittance of the signal beam is measured in a wavelength region of 447-449 nm.

In one embodiment, the gaseous mixture is air, wherein the signal beam is passed through the air with a beam path length of no more than 600 m.

In one embodiment, the reference medium is air, wherein the reference beam is passed through the air with a beam path length of no more than 5.0 m.

In one embodiment, the reference medium is an NO$_2$-free gaseous mixture, wherein the reference beam is passed through the NO$_2$-free gaseous mixture with a beam path length of no more than 100 m.

In one embodiment, a detection limit for the column density of nitrogen dioxide in the gaseous mixture ranges from 0.1-1.0 ppm.m.

In one embodiment, the signal beam is passed through the gaseous mixture with a beam path length of 100-600 m, wherein a detection limit for the concentration of nitrogen dioxide in the gaseous mixture ranges from 0.5-10 ppb.

In one embodiment, the gaseous mixture consists of nitrogen dioxide and nitrogen gas and the reference medium consists of nitrogen gas.

In one embodiment, the gaseous mixture is disposed in an elongated compartment with a length of 0.01-10 m, wherein at least a portion of the elongated compartment is transparent to a UV light and/or a visible light.

In one embodiment, the gaseous mixture is present in the elongated compartment at a pressure of 0.5-1.5 atm.

In one embodiment, the elongated compartment has a length of 0.1-2.0 m, wherein a detection limit for the concentration of nitrogen dioxide in the gaseous mixture ranges from 0.1-10 ppm.

According to a second aspect, the present disclosure relates to a system for measuring a concentration of nitrogen dioxide in a gaseous mixture, the system including i) an elongated compartment with a first end and a second end separated by a side wall along a longitudinal axis of the elongated compartment, wherein at least a portion of the first end and at least a portion of the second end is transparent to a UV light and/or a visible light, ii) at least one sealable aperture arranged on the elongated compartment for delivering a gaseous mixture to the elongated compartment and/or discharging the gaseous mixture from the elongated compartment, iii) a tunable laser diode located at a distance from the elongated compartment for generating a multimode laser beam and emitting the multimode laser beam to the elongated compartment such that the multimode laser beam is substantially parallel to the longitudinal axis of the elongated compartment, iv) a laser diode current controller that is electrically connected to the tunable laser diode for varying an injection current of the tunable laser diode, v) a laser diode temperature controller that is electrically connected to the tunable laser diode for varying a diode temperature of the tunable laser diode, vi) a beam splitter located between the tunable laser diode and the elongated compartment for splitting the multimode laser beam into a signal beam and a reference beam, wherein the signal beam is passed through the gaseous mixture inside the elongated compartment and the reference beam is passed through a reference medium, vii) a first detector for detecting the signal beam after being passed through the gaseous mixture inside the elongated compartment, viii) a second detector for detecting the reference beam after being passed through the reference medium, ix) a computer connected to the first and the second detectors, wherein the computer receives a first voltage signal from the first detector and a second voltage signal from the second detector and calculates the concentration of nitrogen dioxide in the gaseous mixture.

In one embodiment, the tunable laser diode is a multimode blue laser diode that generates a blue laser beam with a wavelength in the range of 445-455 nm.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
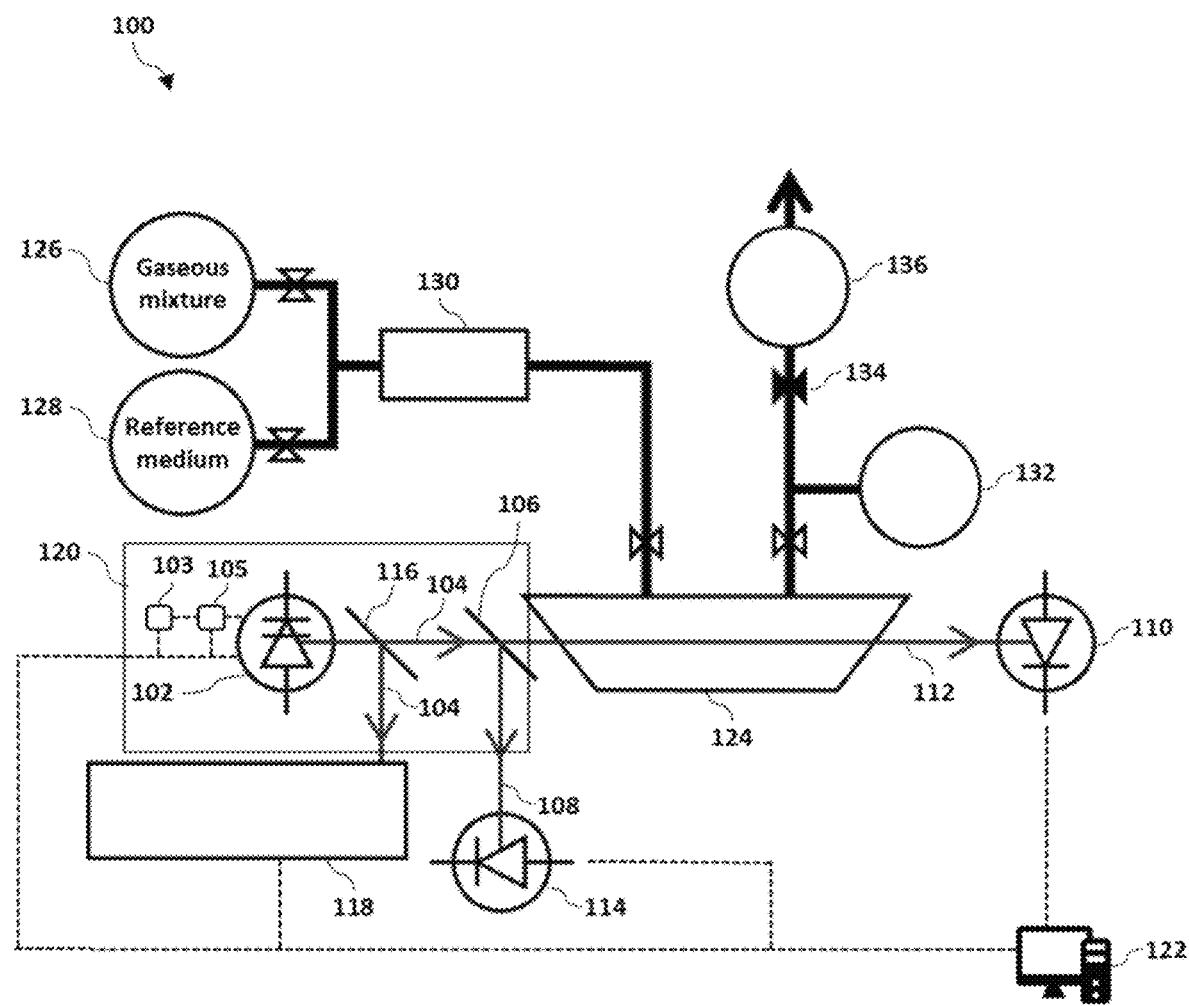
FIG. 1 is a schematic diagram of a system for measuring a concentration of nitrogen dioxide in a gaseous mixture.

Embodiments of the present disclosure will now be described more fully hereinafter with reference to the accompanying drawings, in which some, but not all embodiments of the disclosure are shown.

The present disclosure will be better understood with reference to the following definitions. As used herein, the words "a" and "an" and the like carry the meaning of "one or more." Within the description of this disclosure, where a numerical limit or range is stated, the endpoints are included unless stated otherwise. Also, all values and subranges within a numerical limit or range are specifically included as if explicitly written out.

As used in this disclosure, the term "substantially the same" refers to an embodiment or embodiments where a difference between two quantities are no more than 2%, preferably no more than 1%, preferably no more than 0.5% of the smaller value of the two quantities.

According to a first aspect, the present disclosure relates to a method of measuring a concentration of nitrogen dioxide ($NO_2$) in a gaseous mixture.

The method involves generating a multimode laser beam with a tunable laser diode (LD). In terms of the present disclosure, the "tunable laser diode" refers to a device having a gain medium of a doped semiconductor material as a p-n junction or a p-i-n junction, wherein a gain is generated by an electrical current flowing through the p-n junction or the p-i-n junction. Accordingly, electrons and holes can recombine thereby releasing energy in the form of light photons. In some embodiments, the tunable laser diode may be a semiconductor laser. The multimode laser beam may be generated using other types of lasers, for example, quantum cascade lasers or optically pumped semiconductor lasers. In certain embodiments, the tunable laser diode may be an optical fiber laser with a gain medium comprising an optical fiber doped with one or more rare-earth elements selected from the group consisting of erbium, ytterbium, neodymium, dysprosium, praseodymium, and thulium. In some embodiments, the tunable laser diode may be a quantum-dot type semiconductor laser as known to those skilled in the art. A quantum-dot type semiconductor laser is a type of semiconductor laser that employs a layer of quantum dots as an active gain medium in a light emitting region. Due to a tight confinement of charge carriers in three dimensions, quantum dots may exhibit an electronic structure similar to atoms where energy levels can be adjusted by controlling quantum dot dimensions or quantum dot material compositions. An exemplary quantum-dot type semiconductor laser may be composed of indium gallium arsenide and/or gallium arsenide. The quantum-dot type semiconductor laser may further include an external cavity holographic grating that may stabilize a wavelength of a generated laser beam.

In some embodiments, the tunable laser diode may be selected from one or more laser diodes selected from small edge-emitting LDs, distributed feedback lasers (or DFB lasers), distributed Bragg reflector lasers (DBR lasers), external cavity diode lasers, broad area laser diodes (may alternatively be referred to as broad stripe laser diodes, wide stripe laser diodes, or high brightness laser diodes), slab-coupled optical waveguide lasers (SCOWLs), high-power diode bars, high-power stacked diode bars, and monolithic surface-emitting semiconductor lasers (VCSELs). In a preferred embodiment, the tunable laser diode comprises indium gallium nitride and/or gallium nitride on a silicon carbide substrate. The tunable laser diode may emit the multimode laser beam into a free space, or it may transmit the multimode laser beam to an optical fiber.

In a preferred embodiment, the tunable laser diode generates a coherent narrow-bandwidth light emission whose wavelength is tunable across one or more absorption cross section of $NO_2$ molecules as stated by Yoshino et al [Yoshino, K., Esmond, J. R., Parkinson, W. H., "High-resolution absorption cross section measurements of $NO_2$ in the UV and visible region," Chem. Phys. 221(2), 169-174 (1997)—incorporated herein by reference in its entirety]. Accordingly, in some embodiments, the tunable laser diode is a multimode blue laser diode that generates a coherent narrow-bandwidth light emission whose wavelength is tunable across one or more absorption cross section of $NO_2$ molecules in a wavelength region of 350-500 nm, preferably 400-480 nm, preferably 440-450 nm. For example, in some preferred embodiments, the tunable laser diode is a multimode blue laser diode that generates a blue laser beam with a wavelength in the range of 445-455 nm, preferably 446-450 nm, preferably 447-449 nm. For example, in one embodiment, the tunable laser diode is a Fabry-Perot blue laser diode. In one embodiment, the tunable laser diode is a commercially available blue laser diode obtained from Roithner LaserTechnik GmbH model LD-445-50PD with a power output of up to 50 mW.

The multimode laser beam may preferably cover a tunable spectral range with a width of no more than 5 nm, preferably 1-4 nm, preferably 2-3 nm. As used in this disclosure, the term "tunable spectral range" refers to a wavelength region over which the multimode laser beam can be tuned, for example by varying an injection current of the tunable laser diode. Accordingly, the multimode laser beam may preferably provide a high resolution absorption or transmittance spectrum of the gaseous mixture at an absorption cross section of $NO_2$ molecules in a wavelength region of interest at a width of no more than 5 nm, preferably 1-4 nm, preferably 2-3 nm. Employing the aforementioned multimode laser beam may allow sensitive detection of $NO_2$ in a gaseous mixture at pronounced absorption cross sections of $NO_2$ molecules in the wavelength region 250-650 nm, preferably 350-500 nm, as mentioned by Yoshino et al [Yoshino, K., Esmond, J. R., Parkinson, W. H., "High-resolution absorption cross section measurements of $NO_2$ in the UV and visible region," Chem. Phys. 221(2), 169-174 (1997)—incorporated herein by reference in its entirety]. For example, in a preferred embodiment, the multimode laser beam may cover a tunable spectral range of 445-450 nm, preferably 446-449 nm, preferably 447-449 nm. In another embodiment, the multimode laser beam may cover a tunable spectral range of 421-426 nm, preferably 422-425 nm, preferably 423-425 nm. In still another embodiment, the multimode laser beam may cover a tunable spectral range of 432-438 nm, preferably 433-437 nm. Accordingly, misidentifying absorption signatures that may be recorded in the presence of interferers, e.g. dust particles, in the gaseous mixture may preferably be substantially reduced.

The tunable laser diode may have an output power in the range of 10 mW to 5 W, preferably 20-1,000 mW, preferably 30-500 mW, preferably 40-200 mW, preferably about 50 mW.

In some preferred embodiments, the multimode laser beam is generated at an injection current which is preferably in the range of 30-160 mA, preferably 35-155 mA, preferably 40-150 mA, and a diode temperature which is preferably in the range of 10-60° C., preferably 15-55° C., preferably 20-50° C., preferably 25-50° C. According to these embodiments, the multimode laser beam is preferably generated at a fixed temperature, i.e. 40° C. or 50° C., wherein the injection current is ramped up.

In certain embodiments, an optically non-linear crystal is optically coupled to the tunable laser diode, for example, using optical fibers, wherein the optically non-linear crystal is configured to non-linearly vary a frequency of the multimode laser beam. In addition, in one embodiment, an optical filter may be optically coupled to the optically non-linear crystal, wherein the optical filter is configured to only transmit light photons with a preferable wavelength range, as mentioned previously, while blocking transmission of non-preferable light photons. In certain embodiments, the tunable laser diode may be combined with an external optical resonator, which allows a beam of light to circulate in a closed path. In some embodiments, the tunable laser diode may be combined with additional optics as known to those skilled in the art, such as beam collimators or beam shapers, means for coupling the light to an optical fiber (e.g. fiber-coupled diode lasers), means to provide optical feedback, etc. In certain embodiments, the multimode laser beam is generated with multiple tunable laser diodes and means for beam combining such as, e.g. coherent beam combining devices or spectral beam combining devices as known to those skilled in the art.

Once the multimode laser beam is generated, the method further involves splitting the multimode laser beam into a reference beam and a signal beam with a beam splitter.

The beam splitter is an optical device that splits an incident light beam (e.g. a laser beam) into two or more beams, which may or may not have identical intensities. Any type of the beam splitter as known to those skilled in the art may be utilized here, for example, the beam splitter may be a dielectric mirror, a beam splitter cube, a fiber-optic beam splitter, a metal-coated mirror, a pellicle, a micro-optic beam splitter, a waveguide beam splitter, etc. In one embodiment, the beam splitter is optically coupled to the multimode laser beam at an incidence angle of 30-60°, preferably 35-55°, preferably 40-50°, preferably about 45°. In another embodiment, the beam splitter is a beam splitter cube, which may be made of two triangular glass prisms that are glued together with some transparent resin or cement therebetween. In certain embodiments, crystalline media may be used in lieu of the triangular glass prisms, which allows construction of polarizing beam splitter cubes such as, e.g., Wollaston prisms, Nomarski prisms, Glan-Thompson prisms, Nicol prisms, etc. In another embodiment, the beam splitter is a fiber-optic beam splitter, which is made by fusion-combining of optical fibers. The fiber-optic beam splitter may have more than one output ports.

In a preferred embodiment, the multimode laser beam is split such that the reference beam and the signal beam are substantially the same. Accordingly, the reference beam and the signal beam have substantially the same output powers and substantially the same wavelength ranges.

In some embodiments, the multimode laser beam may be split with a secondary beam splitter before splitting the same with the beam splitter, wherein said split beam is directed to a spectrometer for visualizing and calibrating the multimode laser beam. In one embodiment, the spectrometer consists of a monochromator with a resolution of 0.01-0.05 nm (e.g. SPEX 500M monochromator) and a Thorlabs LC1-USB line camera that are connected to a computer.

In some preferred embodiments, the tunable laser diode and the beam splitter are disposed in a thermally insulated enclosure, which is configured to provide temperature stabilization to the tunable laser diode. In some embodiments, each of the optical components, e.g. the beam splitter, optically non-linear crystals, optical filters, external optical resonators, beam collimators, etc., when present, are disposed in the thermally insulated enclosure. In one embodiment, the thermally insulated enclosure is a commercially available laser diode mount model TCLDM9 provided by Thorlabs.

Figure 2:
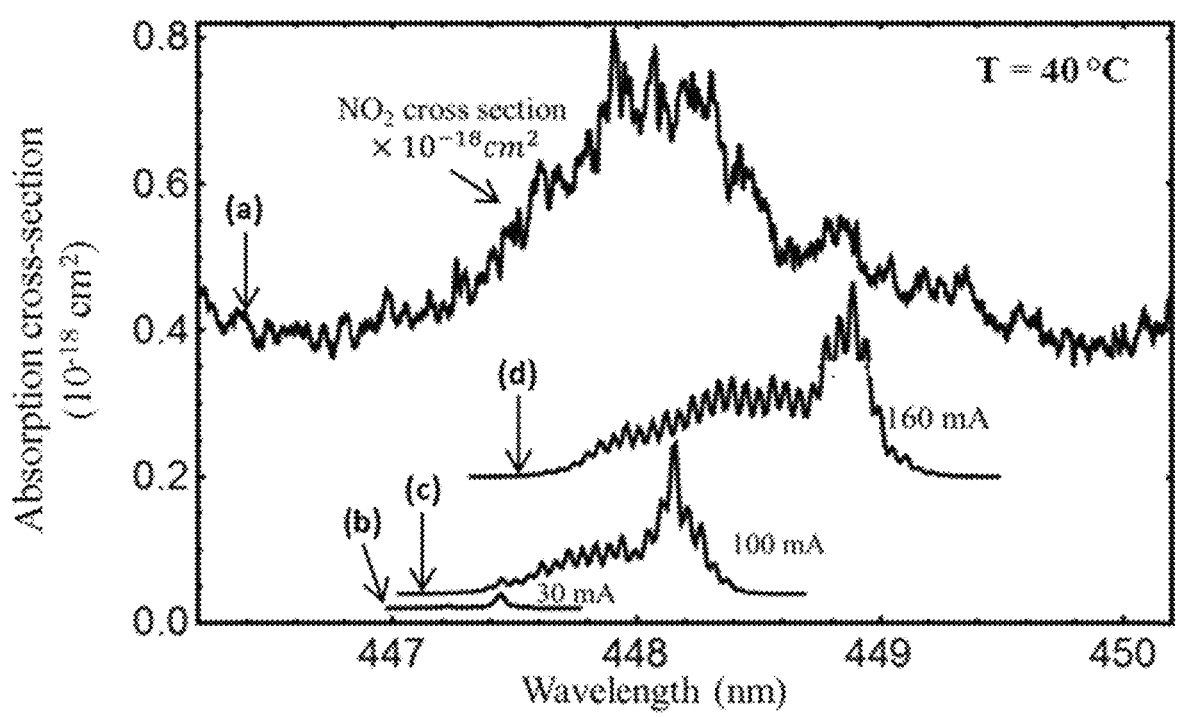
FIG. 2 represents a high resolution absorption spectrum of a laser beam at an absorption cross-section of $NO_2$ in the wavelength region of 446-450 nm, wherein (a) is the absorption cross section of $NO_2$, and the laser beam is generated using (b) a tunable laser diode with an injection current of 30 mA, (c) a tunable laser diode with an injection current of 100 mA, (d) a tunable laser diode with an injection current of 160 mA.

In one embodiment, the tunable laser diode is electrically connected to a laser diode current controller for varying the injection current in the range of 30-160 mA, preferably 35-155 mA, preferably 40-150 mA with an increment of 0.05-0.2 mA, preferably 0.1 mA. As used here, the laser diode current controller is a device that adjusts the injection current of the tunable laser diode. Increasing the injection current of the tunable laser diode at a fixed diode temperature may preferably increase longitudinal modes of the multimode laser diode and may also broaden the spectral range of the multimode laser beam. In one embodiment, the laser diode current controller is a commercially available LDC200C provided by Thorlabs. In one embodiment, the laser diode current controller is in communication with a computer preferably using a LabView and a 16-bit interface card from National Instrument model USB-6251. In some embodiments, increasing the injection current of the tunable laser diode may shift the laser spectra to larger wavelength ranges, as shown in FIG. 2. In view of that, the method may preferably involve tuning the multimode laser beam by varying the injection current of the tunable laser diode in the range of 30-160 mA before splitting the multimode laser beam. In a preferred embodiment, the tunable laser diode includes gallium nitride, which generates a multimode blue laser diode, wherein the blue laser diode is tuned at an injection current resolution of 0.002-0.008 nm/mA, preferably 0.003-0.007 nm/mA, preferably about 0.005 nm/mA. Accordingly, a tuning range of the tunable laser diode by varying the injection current is no more than 0.8 nm, preferably no more than 0.6 nm. The term "injection current resolution" as used herein is a quantity that determines a sensitivity of tuning with respect to varying the injection current. Varying the injection current of the tunable laser diode may allow fine-tuning the absorption spectrum of the multimode laser beam to the wavelength regions of interest, for example, the cross section of $NO_2$ molecules.

In one embodiment, the tunable laser diode is electrically connected to a laser diode temperature controller for varying the diode temperature in the range of 10-60° C., preferably 15-55° C., preferably 20-50° C., preferably 25-50° C., preferably 30-45° C. In one embodiment, the laser diode temperature controller is a commercially available TED200C provided by Thorlabs. The multimode laser beam is temperature sensitive, and diode temperature may influence thermal population distributions in valence and conduction bands in the gain medium of the tunable laser diode. In view of that, the diode temperature of the tunable laser diode is preferably set to a constant value before varying the injection current. In a preferred embodiment, the tunable laser diode includes gallium nitride, which generates a multimode blue laser diode, wherein the blue laser diode is tuned at a temperature resolution of 0.01-0.02 nm/° C., preferably 0.12-0.18 nm/° C., preferably about 0.15 nm/° C. Accordingly, a tuning range of the tunable laser diode by varying the diode temperature is no more than 2 nm, preferably 1-2 nm. The term "temperature resolution" as used herein is a quantity that determines a sensitivity of tuning with respect to varying the diode temperature. Varying the diode temperature of the tunable laser diode may allow tuning the absorption spectrum of the multimode laser beam to the wavelength regions of interest, for example, the cross section of $NO_2$ molecules. In certain embodiments, the laser diode temperature controller includes a thermistor temperature sensor disposed on the tunable laser diode, a thermoelectric cooler element on which the tunable laser diode is mounted, and a micro-controller. In another embodiment, the laser diode temperature controller is in communication with a computer preferably using a LabView and a 16-bit interface card from National Instrument model USB-6251.

Once the multimode laser beam is generated and properly tuned, the method further involves passing the signal beam through the gaseous mixture and recording a first voltage signal with a first detector.

As used in this disclosure, the term "gaseous mixture" refers to a gaseous composition that includes nitrogen dioxide ($NO_2$) and one or more of, without limitation, nitrogen gas, oxygen, carbon dioxide, carbon monoxide, argon, helium, hydrogen, water vapor, nitrogen oxide, methane, neon, krypton, nitrous oxide, sulfur dioxide, etc. In some embodiments, the gaseous mixture only consists of nitrogen dioxide and nitrogen gas. In some embodiments, in order to detect and measure the concentration of $NO_2$ in the gaseous mixture, said concentration is at least 0.5 ppb, preferably at least 1 ppb, preferably at least 5 ppb, preferably at least 10 ppb, preferably at least 50 ppb, preferably at least 100 ppb, preferably at least 200 ppb, preferably at least 500 ppb, preferably at least 1 ppm. In one embodiment, the gaseous mixture is disposed in a closed container (e.g. an elongated compartment) and the signal beam is passed through the gaseous mixture inside the closed container. In one embodiment, the gaseous mixture is delivered to the closed container (e.g. the elongated compartment) in a continuous fashion at a volumetric flow rate of 50-200 ml/min, preferably 80-150 ml/min, preferably about 100 ml/min. In one embodiment, the gaseous mixture is air and the signal beam is passed through the air with a beam path length of no more than 600 m.

The method further involves passing the reference beam through a reference medium and recording a second voltage signal with a second detector.

As used in this disclosure, the term "reference medium" refers to a gaseous composition, which is used for passing the reference beam therethrough. The reference medium may or may not contain nitrogen dioxide depending on the beam path length of the reference beam. For example, in one embodiment, the reference medium is air, which may contain nitrogen dioxide with a concentration of no more than 100 ppm, preferably no more than 50 ppm, preferably no more than 10 ppm, wherein the reference beam is passed through the reference medium with a beam path length of no more than 5.0 m, preferably no more than 2.0 m, preferably no more than 1.0 m. In one embodiment, the reference medium is an $NO_2$-free gaseous mixture, wherein the reference beam may be passed through the $NO_2$-free gaseous mixture with a beam path length of up to 100 m, preferably up to 50 m, preferably up to 10 m. The $NO_2$-free gaseous mixture as used here may refer to a gaseous composition that includes one or more of nitrogen gas, oxygen, carbon dioxide, carbon monoxide, argon, helium, hydrogen, water vapor, nitrogen oxide, methane, neon, krypton, nitrous oxide, sulfur dioxide, and the like, and does not include nitrogen dioxide. The reference medium is preferably of the same composition as the gaseous mixture but for the exclusion of $NO_2$. The reference medium can be obtained by treating the gaseous mixture to remove $NO_2$ thereby providing a reference medium that is of substantially the same composition as the gaseous mixture but for the exclusion of $NO_2$.

The term "beam path length" as used in this disclosure refers to a total distance that a laser beam (e.g. the signal beam or the reference beam) travels from a source (e.g. the beam splitter) to a detector (e.g. the first or the second detector). In circumstances when a laser beam travels in a linear pathway, the beam path length is identical to a distance between the source (e.g. the beam splitter) and the detector (e.g. the first or the second detector).

In a preferred embodiment, each of the first and the second detector is a photodetector having a p-n junction that converts light photons, e.g., laser beam photons into an electric current. Preferably, the first detector is substantially the same as the second detectors, wherein each is a silicon photodiode detector, e.g. Thorlabs model PDB 210A. The first and the second detectors may be in communication with a computer for recording and visualizing the first and the second voltage signals. Various types of photodetectors as known to those skilled in the art may be utilized in lieu of silicon photodiode detectors for recording the first and the second voltage signals. Exemplary include, without limitation, photoemission or photoelectric detectors, thermal photodetectors, polarization detectors, photochemical detectors, weak interaction photodetectors, etc. In certain embodiments, neutral density filters may be utilized to attenuate the signal beam and the reference beam intensities before recording the first and the second voltage signals. In another preferred embodiment, each of the first and the second detector is a photodiode with a p-n junction based on indium arsenide (InAs), indium antimonide (InSb), or mercury cadmium telluride (MCT) that has an electronic response (either as a photocurrent or a voltage) that is sensitive to a UV/Vis light with a wavelength in the range of 250-650 nm, preferably 350-500 nm. Each of the first and the second detector may be provided as a laser module that includes an internal thermo-electric cooler, an internal temperature sensor such as a thermistor, a signal amplifier such as a trans-impedance amplifier that converts current into a proportional voltage, a digitizer, etc. In certain embodiments, the first and the second voltage signals may be amplified to improve a signal-to-noise ratio.

Since the signal beam is passed through the gaseous mixture, the transmittance of the signal beam may provide information about molecular number density C at molecular cross section σ (λ) according to the Lambert-Beer's law. The Lambert-Beer's law states that when a light of intensity $I_0$ (λ) passes through a sample of length L with molecular number density C and molecular cross section σ (λ), an intensity of transmitted light $I_t$ (λ) is given by the following equation:

$$I_t(\lambda) = I_0(\lambda) e^{-\sigma(\lambda) CL} \quad (1)$$

where each of the incident light $I_0$ and the cross section a is a function of the light wavelength λ. Accordingly, if a light is directly detected by an optical detector, such as a photodiode, a signal detected by the optical detector is proportional to an intensity of the light when integrated over the wavelength range of the light.

A transmittance of a light may be measured by two detectors, one for measuring an incident beam (or the reference beam in terms of the present disclosure) and the other for measuring a transmitted beam (or the signal beam in terms of the present disclosure). Accordingly, the measured transmittance T is given by the following equation:

$$T = \frac{\int_{\lambda_s}^{\lambda_e} I_0(\lambda) e^{-\sigma(\lambda) CL} d\lambda}{\int_{\lambda_s}^{\lambda_e} I_0(\lambda) d\lambda} \quad (2)$$

where $\lambda_s$ and $\lambda_e$ are start and end points of the spectral range of the incident light, respectively.

In view of the abovementioned, if a light has a spectral range with a width smaller than one or more features of a cross section σ (λ), and if the light can be tuned over said features, then a variable transmittance may be obtained as a function of a tuning parameter of the light.

In the present disclosure, the multimode laser beam may be tuned by varying the injection current at a fixed diode temperature to produce a variable transmittance as a function of injection current and a signal beam wavelength, λ. Accordingly, at a fixed diode temperature, the transmittance T is a function of an injection current and a signal beam wavelength, λ, as shown in the following equation:

$$T(i) = \frac{\int_{\lambda_s(i)}^{\lambda_e(i)} I_0(\lambda, i) e^{-\sigma(\lambda) CL} d\lambda}{\int_{\lambda_s(i)}^{\lambda_e(i)} I_0(\lambda, i) d\lambda}. \quad (3)$$

Figure 3:
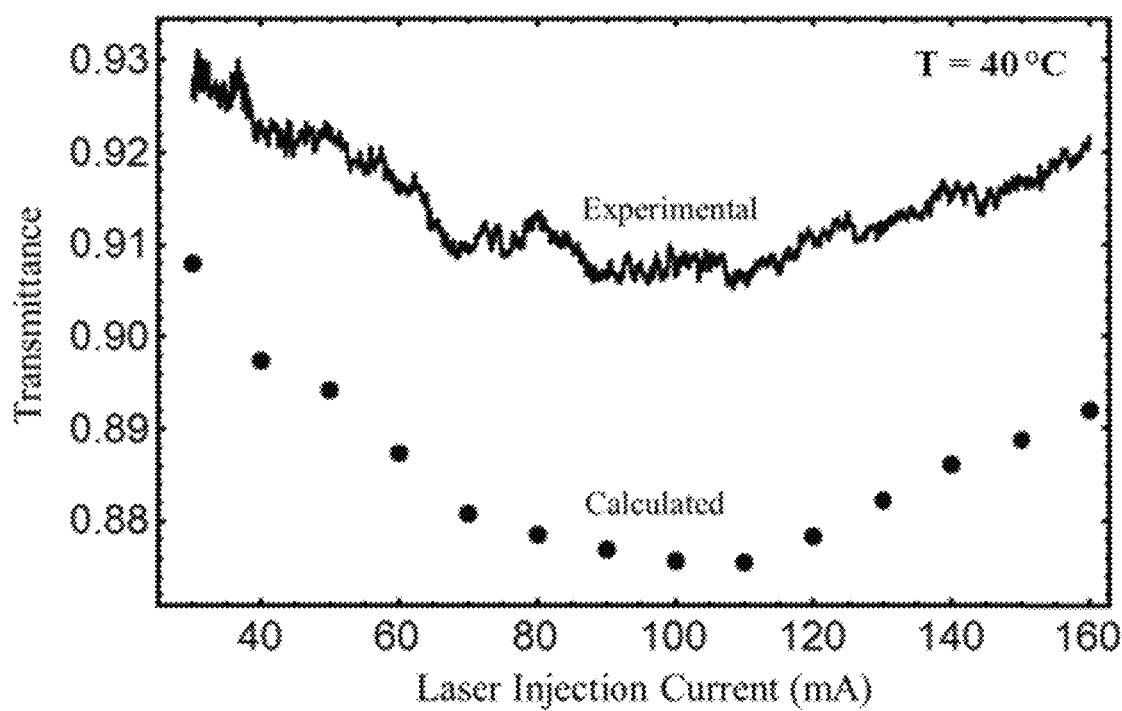
FIG. 3 represents a numerical and an experimental transmittance spectrum of a multimode laser beam through a gaseous mixture, wherein the multimode laser beam is tuned by varying the injection current at a temperature of 40° C.
Figure 4:
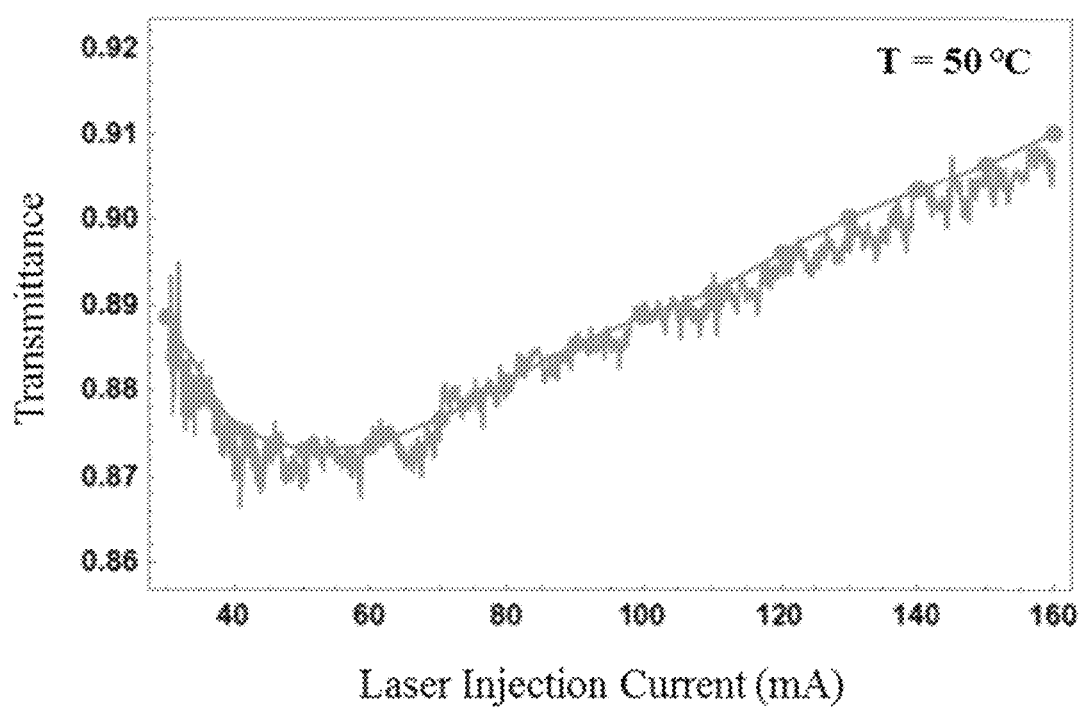
FIG. 4 represents a numerical and an experimental transmittance spectrum of a multimode laser beam through a gaseous mixture, wherein the multimode laser beam is tuned by varying the injection current at a temperature of 50° C.

The shape of the transmittance curve may depend on the diode temperature. To enhance a signal-to-noise ratio in a transmittance spectrum of the signal beam, the diode temperature may be preferably fixed at a temperature in the range of 25-60° C., preferably 30-50° C., preferably 40-50° C., wherein the injection current of the tunable laser diode is ramped up with an increment of 0.05-0.2 mA, preferably 0.1 mA. FIGS. 3 and 4 represent transmittance spectra of a gaseous mixture consisting of nitrogen dioxide and nitrogen gas at various injection currents of the signal beam at a diode temperature of 40° C. and 50° C., respectively.

In cases of small absorptions, for example, in the case of measuring the concertation of $NO_2$ in air, equation (3) can be approximated as:

$$T(i) \cong 1 - CL \frac{\int_{\lambda_s(i)}^{\lambda_e(i)} I_0(\lambda, i) \sigma(\lambda) d\lambda}{\int_{\lambda_s(i)}^{\lambda_e(i)} I_0(\lambda, i) d\lambda}. \quad (4)$$

The column density CL can be measured by fitting the transmittance to the right-hand side of either Eq. 3 or Eq. 4 with CL as a fitting parameter. The ratio of integrals in Eq. 4 may be obtained experimentally by measuring the transmittance of a well-known column density. For example, in one embodiment, the transmittance of a gaseous mixture consisting of nitrogen dioxide and nitrogen gas with a constant $NO_2$ concentration of 200 ppm is measured in a 50 cm column (i.e. a column density CL of 100 ppm.m), and the ratio of integrals in Eq. 4 may be calculated thereafter. In an alternative embodiment, the ratio of integrals in Eq. 4 may be obtained by measuring integrals of the multimode laser beam at a known cross section, σ, which may be obtained from literature at different injection currents.

In view of the present disclosure, to measure the column density CL, the transmittance of the signal beam needs to be measured at various injection currents to produce a high resolution transmittance spectrum, which represents the transmittance of the signal beam through the gaseous mixture as a function of injection current at a fixed diode temperature, as shown in FIGS. 3 and 4.

Accordingly, in a preferred embodiment, the transmittance of the signal beam is measured by taking a ratio of the first voltage signal, which is obtained from the first detector, to the second voltage signal, which is obtained from the second detector. The first voltage signal is obtained from the signal beam, which may preferably be passed through air or the gaseous mixture, as described previously. The second voltage signal is obtained from the reference beam, which may preferably be passed through the reference medium, as described previously. Accordingly, the transmittance may be measured using the following equation:

$$T = \frac{(V)_{gaseous\ mix.}}{(V)_{ref.\ medium}} \quad (5)$$

where $V_{sig}$ and $V_{ref}$ are the voltages of the signal detector and the reference detector, respectively.

In another preferred embodiment, each of the signal beam and the reference beam is normalized before measuring the transmittance. Accordingly, the transmittance of the signal beam is measured by taking a ratio of a first transmittance to a second transmittance, wherein the first transmittance is a ratio of the first voltage signal to the second voltage signal when the signal beam is passed through the gaseous mixture, whereas the second transmittance is ratio of the first voltage signal to the second voltage signal when the signal beam is passed through the reference medium. Accordingly, the transmittance of the signal beam may be measured using the following equation:

$$T = \frac{(V_{sig}/V_{ref})_{gaseous\ mix.}}{(V_{sig}/V_{ref})_{ref.\ medium}} \quad (6)$$

For example, in one embodiment, the gaseous mixture consists of nitrogen dioxide and nitrogen gas and the reference medium consists of nitrogen gas, wherein the transmittance may be measure using the following equation:

$$T = \frac{(V_{sig}/V_{ref})_{NO_2/N_2}}{(V_{sig}/V_{ref})_{N_2}} \quad (7)$$

Once the transmittance of the signal beam is measured at an individual injection current, the multimode laser beam is tuned by varying the injection current of the tunable laser diode. In a preferred embodiment, tuning the multimode laser beam is carried out by increasing the injection current from 30-160 mA, preferably 40-150 mA, with an increment of 0.05-0.2 mA, preferably 0.1 mA. In some embodiment, the increment ranges from 0.5-15 mA, preferably 1-10 mA. In one embodiment, the multimode laser beam is tuned at an injection current resolution of 0.002-0.008 nm/mA, preferably 0.003-0.007 nm/mA, preferably about 0.005 nm/mA. At each individual injection current, the transmittance of the signal beam is measured by following the above-mentioned steps, thereby forming a high resolution transmittance spectrum that represents the transmittance of the signal beam at various injection currents.

Preferably, the multimode laser beam is tuned across one or more pronounced absorption cross sections of $NO_2$ molecules as stated by Yoshino et al [Yoshino, K., Esmond, J. R., Parkinson, W. H., "High-resolution absorption cross section measurements of $NO_2$ in the UV and visible region," Chem. Phys. 221(2), 169-174 (1997)—incorporated herein by reference in its entirety]. Accordingly, in a preferred embodiment, the multimode laser beam is tuned across a wavelength region of 445-450 nm, preferably a wavelength region of 446-449 nm, preferably a wavelength region of 447-449 nm, as shown in FIG. 2. In some preferred embodiments, tuning the multimode laser beam is carried out in a wavelength region with a width of no more than 5 nm, preferably 1-4 nm, preferably 2-3 nm.

The high resolution transmittance spectrum, which may be a function of injection current, is preferably approximated to be proportional to the column density CL and a convolution of an intensity of the multimode laser beam and cross section of $NO_2$ as shown in Eq. 4. Since the high resolution transmittance spectrum has different shapes at different diode temperatures, as shown in FIGS. 3 and 4, a preferred diode temperature may be a temperature at which the high resolution transmittance spectrum produces a more pronounced curvature with a higher signal-to-noise ratio. Accordingly, in a preferred embodiment, the diode temperature is set to a value in the range of 10-60° C., preferably 25-55° C., preferably 35-50° C., more preferably about 40° C.

Once the high resolution transmittance spectrum is obtained, the method further involves measuring the column density CL of nitrogen dioxide in the gaseous mixture using the high resolution transmittance spectrum.

The term "column density" as used here refers to a quantity that measures the number of molecules per unit area projected along a particular line of sight, e.g., a beam path of a laser. In view of that, the term "column density of nitrogen dioxide" as used here refers the number of molecules along a beam path of a laser. Accordingly, the column density of nitrogen dioxide is an integrating a volumetric density of nitrogen dioxide p over the beam path length s of the multimode laser beam as shown in the following equation:

$$CL = \int p \, ds \quad (8)$$

In the case of measuring the concertation of $NO_2$ in the gaseous mixture, e.g. air, the volumetric density of nitrogen dioxide is generally constant over the beam path length of the signal beam. Therefore, the column density CL of nitrogen dioxide is a multiplication of the $NO_2$ concertation in the gaseous mixture (e.g. in ppm) and the beam path length L (e.g. in meter).

According to the present disclosure, the column density CL of nitrogen dioxide may be measured using Eq. 3, preferably using Eq. 4, while taking CL as a fitting parameter. In a preferred embodiment, the column density CL of nitrogen dioxide may preferably be measured using Eq. 4, wherein T(i) is the high resolution transmittance spectrum as a function of the injection current, and the ratio of integrals in Eq. 4 may be obtained experimentally by measuring the transmittance of a well-known column density or by measuring integrals of the multimode laser beam at a known cross section, σ, which may be obtained from literature at different injection currents, as mentioned previously.

In a preferred embodiment, a detection limit for the column density of nitrogen dioxide in the gaseous mixture, when measured by the method of the present disclosure, ranges from 0.1-1.0 ppm.m, preferably 0.2-0.8 ppm.m, preferably 0.3-0.7 ppm.m, preferably 0.4-0.6 ppm.m, more preferably about 0.5 ppm.m.

Once the column density is measured, the method further involves calculating the concentration of nitrogen dioxide in the gaseous mixture from the column density. The concentration of nitrogen dioxide in the gaseous mixture may preferably be calculated by dividing the column density CL by the beam path length L of the signal beam.

According to the abovementioned detection limit ranges for the column density of nitrogen dioxide, in some preferred embodiments, a detection limit for the concentration of nitrogen dioxide in the gaseous mixture ranges from 0.5-10 ppb, preferably 0.6-5 ppb, preferably 0.8-2 ppb, preferably about 1 ppb, when the signal beam travels through the gaseous mixture with a beam path length of 100-600 m, preferably 300-500 m. Yet in some preferred embodiments, a detection limit for the concentration of nitrogen dioxide in the gaseous mixture ranges from 0.1-10 ppm, preferably 0.5-5 ppm, preferably 0.8-2 ppm, preferably about 1 ppm, when the signal beam travels through the gaseous mixture with a beam path length of 0.1-2.0 m, preferably 0.2-1.0 m, preferably about 0.5 m.

In terms of the present disclosure, the term "detection limit" refers to the smallest detectable value of a measurable physical quantity, e.g., the column density CL, the concentration of nitrogen dioxide, etc.

In one embodiment, the gaseous mixture is disposed in an elongated compartment with a length of 0.01-10 m, preferably 0.1-5 m, preferably 0.5-2 m, wherein at least a portion of the elongated compartment is transparent to a UV light and/or a visible light, thus allowing the UV light and/or the visible light to pass therethrough. According to this embodiment, the reference medium may be disposed in a second compartment that is substantially the same as the elongated compartment. In some preferred embodiments, the gaseous mixture is first disposed in the elongated compartment and the first voltage signal is recorded, then the reference medium is disposed in the elongated compartment and the second voltage signal is recorded.

In some preferred embodiments, the gaseous mixture is maintained in the elongated compartment at a pressure of 0.5-1.5 atm, preferably 0.8-1.2 atm, preferably about 1.0 atm. In certain embodiments, the gaseous mixture may be maintained in the elongated compartment at a pressure above 1.5 atm, but preferably no more than 5 atm, preferably no more than 4 atm. In some embodiments, the gaseous mixture is maintained in the elongated compartment at a temperature of 10-70° C., preferably 20-60° C., preferably 30-50° C. The gaseous mixture may have a temperature above 70° C. In these embodiments, the reference medium may preferably be maintained at substantially the same temperatures and pressures.

In some preferred embodiment, the gaseous mixture is delivered to the elongated compartment in a continuous fashion at a volumetric flow rate of 50-200 ml/min, preferably 80-150 ml/min, preferably about 100 ml/min. Various equipment as known to those skilled in the art may be utilized to maintain the pressure of the gaseous mixture in the range of 0.5-1.5 atm, preferably 0.8-1.2 atm, preferably about 1.0 atm. Exemplary equipment may include, without limitation, a vacuum pump such as a roughing pump, a valve such as a needle valve, a pressure gauge such as an absolute capacitance manometer, etc.

In one embodiment, the tunable laser diode and the beam splitter may be located outside of the elongated compartment, wherein the signal beam may be transmitted through a transparent window located on one end of the elongated compartment. As defined herein, "transparent" refers to an optical quality of a material wherein a certain wavelength or range of wavelengths of light may traverse therethrough with a small loss of light intensity. Here, the "transparent window" may causes a loss of less than 5%, preferably less than 2%, more preferably less than 1% of the intensity of the signal beam.

Employing several absorption features (e.g. rotational-vibrational features) using the method of the present disclosure may provide detection of trace molecular species other than nitrogen dioxide, e.g., carbon dioxide, carbon monoxide, nitrous oxide, methane, explosive compounds, steroids, drugs, etc. The detection limit of $NO_2$ concentration using the method of the present disclosure is substantially smaller, for example an order of magnitude smaller, than the detection limit of $NO_2$ concentration when measured using conventional methods such as, for example, direct or wave-modulated absorption spectroscopy. Moreover, the method of the present disclosure offers a shorter data acquisition time period, for example at least 50% shorter, for real-time monitoring of $NO_2$ when compared to conventional methods. Also, since the method of the present disclosure is less expensive due to the absence of expensive laser diodes, e.g. external cavity laser diodes. In view of that, the method of the present disclosure may be applied to analyzers that are utilized in industrial applications for detecting and measuring concentrations of gaseous molecules such as nitrogen dioxide. The method may also be used in monitoring pollutants, e.g. $NO_2$, in the atmosphere.

Referring to FIG. 1, according to a second aspect, the present disclosure relates to a system 100 for measuring the concentration of nitrogen dioxide in a gaseous mixture. The system 100 includes at least a tunable laser diode 102, a laser diode current controller 103, a laser diode temperature controller 105, a beam splitter 106, a first detector 110 and a second detector 114, an elongated compartment 124, a vacuum pump 136 that is fluidly connected to the elongated compartment 124, electronic couplings and gas tubing interconnections, valves, flow controllers, sensors for monitoring temperature, pressure and gas flow rates, and a computer 122. The system 100 may optionally include optical components such as spectrometers, optically non-linear crystals, optical filters, neutral density filters, external optical resonators, beam collimators, etc. In one embodiment, one or more of the tunable laser diode 102, the laser diode current controller 103, the laser diode temperature controller 105, the beam splitter 106, and the abovementioned optical components, when present, are arranged in a thermally insulated enclosure 120. The thermally insulated enclosure 120 may comprise a box fabricated from, for instance, various sheet panels of a thermal insulating material, which provides a temperature-controlled environment for various optical components housed therein. In some embodiments, several temperature sensors (not shown in FIG. 1) may be provided in the thermally insulated enclosure for monitoring an internal temperature of the thermally insulated enclosure. Said temperature sensors may transmit feedback signals to the computer that controls and stabilizes the internal temperature of the thermally insulated enclosure. The thermally insulated enclosure may include one or more heating (or cooling) devices which respond to signals provided by the computer.

In one embodiment, the elongated compartment 124 has a first end and a second end separated by a side wall along a longitudinal axis of the elongated compartment, wherein at least a portion of the first end and at least a portion of the second end is transparent to a UV light and/or a visible light in a wavelength range of 250-650 nm, preferably 350-500 nm. For example, in one embodiment, a transparent window may be present in the first end and the second end, wherein the transparent windows may comprise quartz, glass, or a polymeric material transparent to UV/Vis light such as polymethylmethacrylate (or PLEXIGLAS). In a preferred embodiment, the transparent windows at the first end and the second end may be tilted with an angle of 30-60°, preferably about 45° relative to the longitudinal axis of the elongated compartment, as shown in FIG. 1.

The elongated compartment 124 may have a rectangular shape, preferably a cylindrical shape, or preferably a trapezoidal shape, as shown in FIG. 1. A length of the elongated compartment 124 may vary in the range of 0.01-10 m, preferably 0.1-5 m, preferably 0.5-2 m, and a volume of the elongated compartment 124 may be no more than 10 m$^3$, preferably no more than 1.0 m$^3$, preferably in the range of 1-1000 L (liter), preferably 10-500 L.

In some embodiments, the elongated compartment 124 includes at least one sealable aperture arranged thereon for delivering the gaseous mixture or the reference medium to the elongated compartment and/or discharging the gaseous mixture or the reference medium from the elongated compartment. Accordingly, in one embodiment, the elongated compartment 124 includes one sealable aperture that can be opened and closed, for example, with a valve connected thereto, wherein the sealable aperture is opened during flowing the gaseous mixture or the reference medium to the elongated compartment 124 and is closed during passing the signal beam 112 through the elongated compartment 124. As shown in FIG. 1, in some preferred embodiments, the elongated compartment 124 includes two sealable apertures arranged thereon with two valves for opening and closing each sealable aperture, wherein a first sealable aperture (i.e. an inlet) is configured for delivering the gaseous mixture or the reference medium to the elongated compartment 124 and a second sealable aperture (i.e. an outlet) is configured for discharging the gaseous mixture or the reference medium from the elongated compartment 124. A gas flow controller 130 and several sensors (not shown in FIG. 1) may be installed on the elongated compartment 124 for real-time monitoring of the temperature, the pressure, and/or the flow rate of the gaseous mixture or the reference medium inside the elongated compartment 124. The gaseous mixture may be stored in a first tank, e.g. tank 126, whereas the reference medium may be stored in a second tank, e.g. tank 128. Appropriate utilities such as pipelines, valves, flowrate controllers, etc. as known to those skilled in the art may be employed for selective delivery of the gaseous mixture or the reference medium to the elongated compartment. In some embodiments, a vacuum pump 136 such as a roughing pump, and a needle valve 134 are used for maintaining the gaseous mixture or the reference medium at a preferred pressure range inside the elongated compartment 124. A pressure gauge 132 may be used for real-time monitoring the pressure of the gaseous mixture or the reference medium inside the elongated compartment 124.

The system 100 further includes a tunable laser diode 102, as described previously, located at a distance from the elongated compartment 124 for generating a multimode laser beam 104 and emitting the multimode laser beam 104 to the elongated compartment 124. In one embodiment, the tunable laser diode 102 is arranged such that the multimode laser beam 104 is substantially parallel to the longitudinal axis of the elongated compartment 124, as shown in FIG. 1. The distance between the tunable laser diode 102 and the elongated compartment 124 may be preferably no more than 1 m, preferably 10-80 cm, preferably 20-50 cm. The beam splitter 106, which is arranged in the distance between the tunable laser diode 102 and the elongated compartment 124, preferably reflects a first portion of the multimode laser beam 104, i.e. the reference beam 108, downwardly to the second detector 114, whereas a second portion of the multimode laser beam 104, i.e. the signal beam 112, travels through the beam splitter 106 and enters the elongated compartment 124, as shown in FIG. 1. Upon leaving the elongated compartment 124, the signal beam 112 may hit the first detector 110. In one embodiment, the system includes a secondary beam splitter 116 that splits a portion of the multimode laser beam 104 to the spectrometer 118 for visualizing and/or calibrating the multimode laser beam 104.

The system 100 further includes a laser diode current controller 103 and a laser diode temperature controller 105, as described previously, wherein each is electrically connected to the tunable laser diode 102 for varying the injection current and the diode temperature of the tunable laser diode 102. In one embodiment, the laser diode current controller 103 is a commercially available LDC200C provided by Thorlabs, which is in communication with the computer 122 preferably with a LabView and a 16-bit interface card from National Instrument model USB-6251. In another embodiment, the laser diode temperature controller 105 is a commercially available TED200C provided by Thorlabs, which is in communication with the computer 122 preferably with a LabView and a 16-bit interface card from National Instrument model USB-6251.

The system 100 further includes the first detector 110 for detecting the signal beam 112 after being passed through the gaseous mixture inside the elongated compartment 124. In addition, the system 100 further includes the second detector 114 for detecting the reference beam 108 after being passed through the reference medium. The type of the first and the second detector s are not meant to be limiting and various detectors, as described previously, may be utilized here. For example, in a preferred embodiment, the first and the second detectors are substantially the same, wherein each is a silicon photodiode detector, e.g. Thorlabs model PDB210A, which is in communication with the computer 122. Each of the first and the second detector may be provided as a package that includes an internal thermo-electric cooler, an internal temperature sensor such as a thermistor, a signal amplifier such as a trans-impedance amplifier that converts current into a proportional voltage, a digitizer, etc.

The system 100 further includes the computer 122 that is connected to the first detector 110 and the second detector 114, wherein the computer 122 receives a first voltage signal from the first detector 110 and a second voltage signal from the second detector 114 and calculates the concentration of nitrogen dioxide in the gaseous mixture. The computer 122 may be used for one or more of controlling the injection current and the diode temperature of the tunable laser diode, calibrating the multimode laser beam, controlling and monitoring the flow rate, the temperature, and the pressure of the gaseous mixture or the reference medium in the elongated compartment, controlling and monitoring the temperature inside the thermally insulating enclosure, etc.

In some embodiments, the computer 122 may include one or more components of a personal or desk computer including a motherboard with a microprocessor, cache memory, ROM memory, random access memory such as a hard disk, optical disk drive or flash memory, an operating system, control software, various external communication ports at its front and rear panels for sending information to and receiving information from the computer. Example of such external communication ports may include Universal Serial Bus (USB) ports for connecting a keyboard, an external memory device, etc. to the computer; an Ethernet port for connecting the computer to an external network or to other computers and a VGA/HDMI port for providing detailed visual information display to a user.

The examples below are intended to further illustrate protocols for the method of measuring the concentration of $NO_2$ in a gaseous mixture, and are not intended to limit the scope of the claims.

EXAMPLE 1

The following examples illustrate a method to identify and measure the absorption of $NO_2$ over a wavelength range of few nanometers using a tunable Fabry-Perot multimode blue laser diode.

According to the Lambert-Beer's law, when a light of intensity $I_0(\lambda)$ passes through a sample of length L with molecular number density C and molecular cross section $\sigma(\lambda)$, the intensity of transmitted light $I_t(\lambda)$ may be measured by the following equation:

$$I_t(\lambda) = I_0(\lambda) e^{-\sigma(\lambda) CL} \tag{1}$$

where the incident light, the transmitted light and the cross section are all functions of the light wavelength $\lambda$. If the light is directly detected by an optical detector, such as a photodiode, the signal registered by the detector is proportional to the intensity integrated over the wavelength range of the light. Hence, if the transmittance is measured by two detectors, one measuring the incident beam and the other measuring the transmitted beam, the measured transmittance T is given by the following equation:

$$T = \frac{\int_{\lambda_s}^{\lambda_e} I_0(\lambda) e^{-\sigma(\lambda)CL} d\lambda}{\int_{\lambda_s}^{\lambda_e} I_0(\lambda) d\lambda} \quad (2)$$

where $\lambda_s$ and $\lambda_e$ are the start and end of the spectral range of the incident light, respectively. Here, we assume the detector efficiencies are constant as we will use small tuning ranges of about 2 nm. If the light source has a spectral width smaller than some features of the cross section $\sigma(\lambda)$, and if the light source can be tuned over these features, then one can obtain a varying transmittance as a function of the tuning parameters of the light source. This varying transmittance provides a unique signature of the investigated molecule.

The $X^2A_1 \rightarrow A^2B_2$ visible absorption band of $NO_2$ extends from about 300 to 600 nm peaking around 400 nm with a relatively large cross section of about $6 \times 10^{-19}$ cm$^2$. Although, individual spectral lines of this band are not resolvable at ambient atmospheric pressure due to collisional broadening, there are many relatively sharp features some of which with a relative variation as large as 60% and a full-width-half-maximum of about one nm, such as that around 448 nm which we will use.

A typical laser diode can be used to obtain significant variations in absorption as it is tuned over a specific feature of the $NO_2$ visible band. A typical blue laser diode, operating well above threshold, has many longitudinal modes, more than 20 modes, and its modes cover a spectral range of about one nm. The spectral range starts just above threshold with a fraction of one nm with one or two longitudinal modes and widens in range to about two nm as the injection current is increased. In addition, the range also shifts toward higher wavelength with the injection current. The spacing between two adjacent longitudinal modes is typically 0.05 nm and is given by $\Delta\lambda = \lambda^2/2nL$, where $\lambda$ is the wavelength, n≅3 is the index of refraction of the gain medium of the laser, gallium nitride, and L is the length of the laser cavity typically 600 μm. The laser modes can be tuned rapidly by varying the injection current or can be tuned at slower rate by altering the temperature. Typically, a mode can by tuned at rate of about 0.005 nm/mA and 0.015 nm/° C. toward longer wavelengths. This corresponds to a tuning range of a specific mode about 0.6 nm for the allowed maximum injection current range of 130 mA and a tuning range of about one nm for the allowed maximum range of temperature of 60° C. See for example [Romadhon, M. S., Aljalal, A., Al-Basheer, W., Gasmi, K., "Longitudinal modes evolution of a GaN-based blue laser diode," Opt. Laser Technol. 70, 59-62, Elsevier Ltd (2015)—incorporated herein by reference in its entirety].

The temperature of laser diode can be adjusted so that the tuning range by current produces the most pronounced variation in the transmittance. Hence, the transmittance T is a function of the laser current, as well as the laser spectrum, the start and the end of the laser spectrum range, as shown in the following equation:

$$T(i) = \frac{\int_{\lambda_s(i)}^{\lambda_e(i)} I_0(\lambda, i) e^{-\sigma(\lambda)CL} d\lambda}{\int_{\lambda_s(i)}^{\lambda_e(i)} I_0(\lambda, i) d\lambda}. \quad (3)$$

For very small absorptions, as in the case of monitoring $NO_2$ in ambient air, equation (3) can be approximated by the following equation:

$$T(i) \cong 1 - CL \frac{\int_{\lambda_s(i)}^{\lambda_e(i)} I_0(\lambda, i) \sigma(\lambda) d\lambda}{\int_{\lambda_s(i)}^{\lambda_e(i)} I_0(\lambda, i) d\lambda}. \quad (4)$$

Thus, the column density CL can be measured by fitting the measured transmittance to the right-hand side of either Eq. 3 or Eq. 4 with CL as the fitting parameter. The ratio of integrals in Eq. 4 was obtained experimentally by measuring the transmittance of a well-known column density. The ratio of integrals can alternatively be obtained by integrating the spectra of the laser that is obtained at different injection currents, wherein the cross section can be obtained from literature.

The shape of the transmittance curve as function of the laser current depends on the laser diode temperature. In order to enhance the signal-to-noise ratio, the temperature was set to a preferred temperature (e.g. 40° C. or 50° C.) to obtain a curve with the biggest variation. A detection limit for column density of about 0.5 ppm.m was achieved with short integration time, which corresponds to a detection limit of about 1 ppm for a length of 50 cm.

EXAMPLE 2

FIG. 1 shows a schematic diagram of the experimental setup. A blue laser diode Roithner LaserTechnik GmbH model LD-445-50PD is utilized, which has a nominal output wavelength of 445 nm with an output power of up to 50 mW. The laser diode was housed in a laser diode mount model TCLDM9 from Thorlabs. The injection current and the diode temperature were controlled using Thorlabs LDC200C and TED200C controllers, respectively. Both controllers were connected to a PC using a LabView VI and a 16-bit interface card from National Instrument model USB-6251.

To measure the spectrum of the laser, part of the laser beam was directed to a spectrometer that includes a SPEX 500M monochromator and a Thorlabs LC1-USB line camera. The monochromator has a resolution of 0.02 nm and the wavelength of the monochromator is calibrated with seven spectral lines from a Kr discharge lamp. The laser spectra are collected at injection currents ranging from 30 mA to 160 mA in a step of 10 mA. This measurement has to be done only once at a specific laser temperature.

Before entering the elongated compartment, part of the laser beam was directed to a silicon photodiode detector from Thorlabs model PDB 210A. This beam was used to normalize the laser intensity variation and thus is called the reference beam. The rest of the laser beam, i.e. the signal beam, was passed through the elongated compartment and further detected by another silicon photodiode detector model PDB 210A. Both detectors were connected to the PC with a USB-6251 interface. Neutral density filters were also used to attenuate the laser beam intensities. For the transmittance measurements, the laser temperature was fixed, and readings from both detectors were recorded at each step of the laser injection current in the range from 30 mA to 160 mA in a step of 0.1 mA.

The elongated compartment has a length of 40 cm and was made from stainless steel. The elongated compartment windows were tilted to eliminate interferences due to the windows' surfaces. A $NO_2/N_2$ gas mixture with an $NO_2$ concentration of 200 ppm was flowed into the elongated compartment in a controlled flow rate using a mass flow controller, Omega FMA5412A-ST. Also a high purity $N_2$ gas was flowed into the elongated compartment in a controlled flow rate using a mass flow controller, Omega FMA5412A-ST. The gas flow rate was controlled to reduce the effect of $NO_2$ adsorption on the surface of the elongated compartment. The pressure in the elongated compartment was maintained at atmospheric pressure using a roughing pump, a needle valve, and an absolute capacitance manometer model MKS 690A13TRA.

EXAMPLE 3

FIG. 2 shows the absorption cross section of $NO_2$ molecules [Yoshino, K., Esmond, J. R., Parkinson, W. H., "High-resolution absorption cross section measurements of $NO_2$ in the UV and visible region," Chem. Phys. 221(2), 169-174 (1997)1, and three spectra of the laser beam at a laser temperature of 40° C. and a wavelength region that the laser used here can be tuned. The laser tuning range is from about 447.2 nm to 449.2 mm, which covers one of the most pronounced features of $NO_2$ cross section at 448 nm. The fractional variation $((\sigma_{max}-\sigma_{min})/\sigma_{avg})$ of this feature is about 0.60 with full-width-half-maximum of 0.8 nm. FIG. 2 shows the three spectra of the laser, one at an injection current of 30 mA just at the laser threshold, one at an injection current of 100 mA, and the last one at an injection current of 160 mA, which corresponds to the maximum allowable injection current. As the injection current increases, the laser spectrum becomes wider and shifts toward higher wavelengths.

The continuous curve in FIG. 3 is the measured transmittance of the $NO_2/N_2$ gas mixture with the $NO_2$ concentration of 200 ppm. To obtain the transmittance, two separate measurements were used, one for normalization, when pure $N_2$ gas was flowed into the elongated compartment, and the other when the $NO_2/N_2$ gas mixture was flowed into the elongated compartment. Hence, the measured transmittance T is given by the following equation:

$$T = \frac{(V_{sig}/V_{ref})_{NO_2/N_2}}{(V_{sig}/V_{ref})_{N_2}} \quad (5)$$

where $V_{sig}$ and $V_{ref}$ are the voltages of the signal detector and the reference detector, respectively. FIG. 3 also shows the calculated transmittance obtained from the cross section of $NO_2$ and measured laser spectra using Eq. 3 with a column density of CL 200 ppm×40 cm, in accordance with our experiment parameters.

Although the measured and calculated transmittance spectra revealed the same curvature with a minimum value at a laser injection current of about 100 mA, there is a difference between the two transmittance spectra. The difference may happen due to the adsorption of a portion of $NO_2$ molecules on the surface of the elongated compartment. In these measurements, a flow rate of 100 ml/min was utilized. Another probable reason for the mismatch between the measured and calculated transmittance spectra may be due to the inaccuracy of $NO_2$ concentration in the $NO_2/N_2$ gas mixture as claimed by the vendor. However, the insignificant mismatch does not reject the notion that a regular multimode blue laser diode can be used to identify $NO_2$ by providing transmittance over a range of wavelengths and, hence, reducing the chance of misidentifying absorption from $NO_2$ with absorption from other broadband interferers such dust particles.

From the range of variation and the noise level in the experimental transmittance, a detection limit of 2 ppm over a length of 40 cm is estimated. This detection limit corresponds to a detection limit of about 2 ppb over a distance of 400 m, which makes the method of the present disclosure suitable for detecting $NO_2$ pollution over long paths.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method of measuring a concentration of nitrogen dioxide in a gaseous mixture, comprising:
    generating a multimode laser beam with a tunable laser diode at an injection current and a diode temperature;
    splitting the multimode laser beam into a reference beam and a signal beam with a beam splitter optically coupled to the multimode laser beam at an incidence angle of 30-60°;
    passing the signal beam through the gaseous mixture and recording a first voltage signal with a first detector;
    passing the reference beam through a reference medium and recording a second voltage signal with a second detector;
    measuring a transmittance of the signal beam at the injection current, wherein the transmittance is a ratio of the first voltage signal to the second voltage signal;
    tuning the multimode laser beam by varying the injection current and repeating the splitting, passing the signal beam, passing the reference beam, and the measuring to form a transmittance spectrum;
    measuring a column density of nitrogen dioxide in the gaseous mixture from the transmittance spectrum; and
    calculating the concentration of nitrogen dioxide in the gaseous mixture from the column density;
    wherein the gaseous mixture is disposed in an elongated compartment having a length of 0.01-10 m and a first end and a second end,
    wherein the first end and the second end each have a transparent window transparent to a UV light and/or a visible light,
    wherein the transparent windows are tilted with an angle of 30-60° relative to a longitudinal axis of the elongated compartment, and
    wherein each transparent window causes a loss of less than 1% of the intensity of the signal beam.

2. The method of claim 1, wherein the multimode laser beam has a wavelength in the range of 250-650 nm.

3. The method of claim 1, wherein the multimode laser beam is a blue laser beam with a wavelength in the range of 445-455 nm.

4. The method of claim 1, wherein the multimode laser beam covers a tunable spectral range with a width of no more than 5 nm, and
wherein the tuning is carried out in a wavelength region with a width of no more than 5 nm.

5. The method of claim 1, wherein the tuning is carried out by increasing the injection current from 30 mA to 160 mA with increments in the range of 0.05-0.2 mA.

6. The method of claim 5, wherein the multimode laser beam is tuned at an injection current resolution of 0.002-0.008 nm/mA.

7. The method of claim 1, wherein the diode temperature is set to a value in the range of 10-60° C. before the splitting.

8. The method of claim 1, wherein the transmittance of the signal beam is measured in a wavelength region of 445-450 nm, and
wherein the transmittance is in a range of 87-93%.

9. The method of claim 1,
wherein the gaseous mixture is air.

10. The method of claim 1, wherein the reference medium is an $NO_2$-free gaseous mixture.

11. The method of claim 1,
wherein the reference medium is air, and
wherein the reference beam is passed through the air with a beam path length of no more than 5.0 m.

12. The method of claim 1, wherein the gaseous mixture consists of nitrogen dioxide and nitrogen gas and the reference medium consists of nitrogen gas.

13. The method of claim 1, wherein the gaseous mixture is present in the elongated compartment at a pressure of 0.5-1.5 atm.

14. The method of claim 1, wherein the elongated compartment has a length of 0.1-2.0 m.

* * * * *